United States Patent [19]
Davis et al.

[11] Patent Number: 5,620,876
[45] Date of Patent: Apr. 15, 1997

[54] ENZYMATIC HYDROLYSIS AND ESTERIFICATION PROCESSES FOR THE PREPARATION OF HMG-COA REDUCTASE INHIBITORS AND INTERMEDIATES THEREOF

[75] Inventors: Brian L. Davis, Dayton; Paul M. Cino, Bound Brook; Laszlo J. Szarka, East Brunswick, all of N.J.

[73] Assignee: E. R. Squibb & Sons, Inc., Princeton, N.J.

[21] Appl. No.: 875,859

[22] Filed: Apr. 29, 1992

[51] Int. Cl.$^6$ ............................ C12P 7/40; A61K 31/425
[52] U.S. Cl. ...................... 435/136; 514/365; 549/292
[58] Field of Search ..................... 514/365; 435/136; 549/292

[56] References Cited

U.S. PATENT DOCUMENTS

| | | | |
|---|---|---|---|
| 3,983,140 | 9/1976 | Endo et al. | 549/292 |
| 4,346,227 | 8/1982 | Terahara et al. | 560/119 |
| 4,444,784 | 4/1984 | Hoffman et al. | 514/460 |

FOREIGN PATENT DOCUMENTS

0486153A2  5/1992  European Pat. Off. .

60-176595  9/1985  Japan .

OTHER PUBLICATIONS

Editor: Ebel "Biotechnology and Biotransformations" 1984 p. 48 148–164, 253–267.

Komagata et al., "Microbial Conversion of Compactin (ML–236B) to ML–236A", pp. 1574–1577, *J. of Antibiotics*, Nov. 1986.

Conder et al., abstract of Poster No. A2 titled "Discovery and Purification of an Esterase from Clonostachys Compactiuscula Useful for the Biotransformation of Lovastatin Acid to Triol Acid", presented at Biocatalysis for the 90s, An International Conference on the New Science and Techniques for the Discovery, Design and Use of Biocatalysts, Jun. 5–7, 1991, Lake Buena Vista, Florida.

*Primary Examiner*—Michael G. Wityshyn
*Assistant Examiner*—Francisco C. Prats
*Attorney, Agent, or Firm*—Burton Rodney

[57] ABSTRACT

Enzymatic hydrolysis and esterification processes for the preparation of compounds useful as HMG-CoA reductase inhibitors and/or as intermediates in the preparation of HMG-CoA reductase inhibitors.

7 Claims, No Drawings

ENZYMATIC HYDROLYSIS AND ESTERIFICATION PROCESSES FOR THE PREPARATION OF HMG-COA REDUCTASE INHIBITORS AND INTERMEDIATES THEREOF

FIELD OF THE INVENTION

The present invention relates to enzymatic hydrolysis and esterification processes for the preparation of compounds useful as HMG-CoA reductase inhibitors and/or as intermediates in the preparation of HMG-CoA reductase inhibitors.

SUMMARY OF THE INVENTION

The present invention provides a method for the preparation of a compound of the formula I:

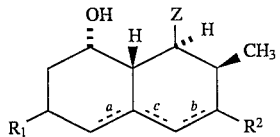

where
Z is the lactone:

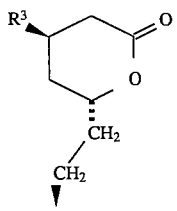

or the open chain moiety:

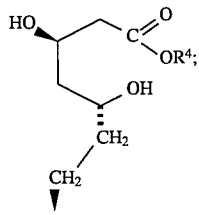

$R^1$ and $R^2$ are independently selected from:
  (i) hydrogen;
  (ii) hydroxyl;
  (iii) alkoxy, especially methoxy;
  (iv) alkyl, especially methyl;
  (v) —$OSO_2H$; or
  (vi) if not already included above, protected hydroxyl;
$R^3$ is hydroxyl or protected hydroxyl;
$R^4$ is hydrogen; a pharmaceutically acceptable cation; or a moiety which, together with the atoms to which it is bonded, forms a pharmaceutically acceptable ester group; and
a, b and c represent optional double bonds which double bonds, when any are present, are a and b in combination or a, b or c alone;
or a salt thereof;
  comprising the step of contacting a compound of the formula II:

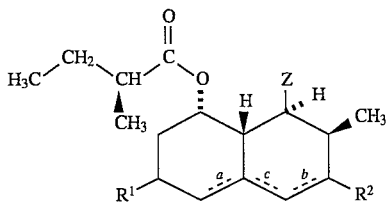

where Z, $R^1$, $R^2$, a, b and c are as defined in formula I, or a salt thereof, with a microorganism, or with an enzyme derived from, or having the structure of an enzyme derived from, said microorganism, which is capable of catalyzing the hydrolysis of said compound of the formula II to yield said compound of the formula I, and effecting said hydrolysis;
  where said microorganism is selected from the genera *Penicillium*, *Kibdelosporangium*, *Chaetomium*, *Aspergillus*, *Emericella*, *Daldinia*, *Hypoxylan*, *Neurospora*, *Podospora*, *Sordaria*, *Xylaria*, *Cephalosporium*, *Gliocladium*, *hypocrea*, *Nectria*, or *Trichoderma*.

The enzymatic hydrolysis process of the present invention provides an efficient means for obtaining compounds of the formula I, which may themselves exhibit HMG-CoA reductase inhibitory activity, and/or which may be used as intermediates in the preparation of HMG-CoA reductase inhibitors. Reduction or elimination of by-products may be achieved by employing the hydrolysis method of the present invention, which method may also be conducted under mild reaction conditions.

The present invention also provides a method for the preparation of a compound of the formula II:

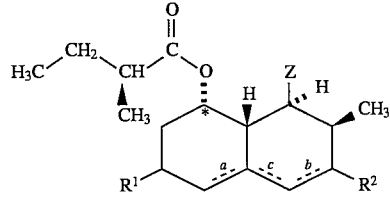

where
Z is the lactone

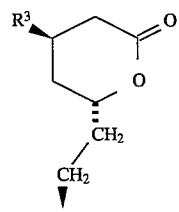

or the open chain moiety:

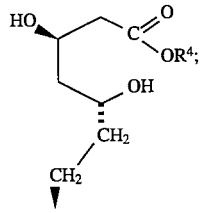

$R^1$ and $R^2$ are independently selected from:
  (i) hydrogen;
  (ii) hydroxyl;
  (iii) alkoxy, especially methoxy;

3

(iv) alkyl, especially methyl;

(v) —OSO$_2$H; or (vi) if not already included above, protected hydroxyl;

R$^3$ is hydroxyl or protected hydroxyl;

R$^4$ is hydrogen; a pharmaceutically acceptable cation; or a moiety which, together with the atoms to which it is bonded, forms a pharmaceutically acceptable ester group; and a, b and c represent optional double bonds which double bonds, when any are present, are a and b in combination or a, b, or c alone; or a salt thereof;

comprising the step of contacting a compound of the formula I:

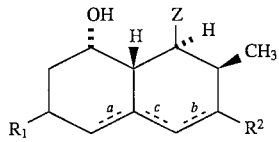

where Z, R$^1$, R$^2$, a, b, and c are as defined in formula II, or a salt thereof, with a compound of the formula III:

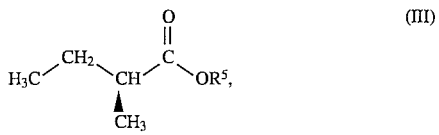

where R$^5$ is hydrogen, or alkyl such as methyl, and with a microorganism, or with an enzyme derived from, or having the structure of an enzyme derived from, said microorganism, which is capable of catalyzing the esterification of said compound of the formula I to yield said compound of the formula II, and effecting said esterification;

where said microorganism is selected from the genera *Penicillium, Kibdelosporangium, Chaetomium, Aspergillus, Emericella, Daldinia, Hypoxylan, Neurospora, Podospora, Sordaria, Xylaria, Cephalosporium, Gliocladium, Hypocrea, Nectria*, or *Trichoderma*.

The enzymatic esterification process of the present invention provides an efficient, site-specific, stereoselective means for obtaining compounds of the formula II having a 2-methylbutyrate side chain in the stereochemical position indicated at the chiral center marked with an asterisk in formula II. That is, in the present process, compounds of the formula II in which the methylbutyrate side chain is attached below the plane of the ring system nucleus are formed preferentially to, or, preferably, to the total exclusion of, compounds in which the methylbutyrate side chain is attached above the plane of the ring system nucleus.

The compounds of formula II may exhibit HMG-CoA reductase inhibitory activity and/or may be used as intermediates in the preparation of HMG-CoA reductase inhibitors.

DETAILED DESCRIPTION OF THE INVENTION

The methods of the present invention are described further as follows.

DEFINITIONS

The terms "enzymatic process" or "enzymatic method" as used herein denote a process or method of the present invention employing an enzyme or microorganism.

4

The terms "alkyl", "alkan" or "alk" as employed herein alone or as part of another group preferably denote both straight and branched chain, optionally substituted hydrocarbons containing 1 to 15 carbons in the normal chain, preferably 1 to 6 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Exemplary substituents may include one or more groups selected from the following: halo (especially chloro), trihalomethyl, alkoxy (for example, where two alkoxy substituents form an acetal), aryl such as unsubstituted aryl (e.g. phenyl), alkyl-aryl or haloaryl, cycloalkyl such as unsubstituted cycloalkyl or alkyl-cycloalkyl, hydroxy or protected hydroxy, carboxyl, alkyloxycarbonyl, alkylamino, dialkylamino such as dimethylamino, alkylcarbonylamino such as acetylamino, amino, arylcarbonylamino, nitro, cyano, thiol, or alkylthio. Preferred alkyl substituents are hydroxyl groups.

The term "alkenyl", as employed herein alone or as part of another group, preferably denotes optionally substituted groups as described above for alkyl, further containing at least one carbon to carbon double bond.

The term "cycloalkyl", as employed herein alone or as part of another group, preferably denotes an optionally substituted, saturated homocyclic carbon ring system, most preferably containing from 1 to 3 rings and from 3 to 12, such as from 3 to 8 carbons per homocyclic ring such as cyclopropyl, cyclobutyl, cyclopentyl, cyclohexyl, cycloheptyl, cyclooctyl, cyclodecyl, cyclododecyl, and adamantyl. Exemplary optional substituents include one or more alkyl groups as described above, or one or more of those groups described above as alkyl substituents.

The terms "aryl" or "ar" as employed herein preferably denote monocyclic or bicyclic substituted or unsubstituted aromatic groups containing from 6 to 12 carbons in the ring portion, such as phenyl, biphenyl, naphthyl substituted phenyl, substituted biphenyl or substituted naphthyl. Exemplary substituents (preferably three or fewer) include one or more of the following groups: alkyl such as unsubstituted alkyl, haloalkyl, or cycloalkylalkyl, halogen, alkoxy such as unsubstituted alkoxy or haloalkoxy, hydroxy, aryl such as phenyl or halophenyl, aryloxy such as phenoxy, alkylcarbonyloxy or aroyloxy, allyl, cycloalkyl, alkylamino, dialkylamino, amido such as alkylcarbonylamino or arylcarbonylamino, amino, nitro, cyano, alkenyl, thiol, alkylcarbonyl, or arylcarbonyl, or methylenedioxy where the methylene group may be substituted by lower alkyl group(s) (that is, alkyl groups as described above having 1 to 6 carbon atoms), arylalkenyl group(s), and/or alkylthio group(s).

The terms "halo" or "halogen" as used herein denote chlorine, fluorine, bromine or iodine.

The term "hydroxyl protecting group" as used herein denotes a group capable of protecting a free hydroxyl group which, subsequent to the reaction for which protection is employed, may be removed without disturbing the remainder of the molecule. A variety of protecting groups for the hydroxyl group and the synthesis thereof may be found in "Protective Groups in Organic Synthesis" by T. W. Greene, John Wiley and Sons, 1981, or Fiser & Fiser. Exemplary hydroxyl protecting groups include methoxymethyl, 1-ethoxyethyl, benzyloxymethyl, (β-trimethylsilylethoxy)methyl, tetrahydropyranyl, 2,2,2-trichloroethoxycarbonyl, t-butyl(diphenyl)silyl, trialkylsilyl such as t-butyl(dimethyl)silyl, trichloromethoxycarbonyl and 2,2,2-trichloroethoxymethyl.

The term "salt(s)" as employed herein refers to acidic and/or basic salts formed with inorganic and/or organic bases. The nontoxic, pharmaceutically acceptable salts are preferred. Exemplary pharmaceutically acceptable salts include those formed from cations such as sodium, potassium, aluminum, calcium, lithium, magnesium, zinc and tetramethylammonium as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine and tris(hydroxymethyl)aminomethane.

The term "pharmaceutically acceptable cation" denotes a positive counterion forming a pharmaceutically acceptable salt, such as those described above.

The term "a moiety which, together with the atoms to which it is bonded, forms a pharmaceutically acceptable ester group" preferably denotes an optionally substituted alkyl moiety such as unsubstituted $C_{1-4}$ alkyl or phenyl-, dimethylamino- or acetylamino-substituted $C_{1-4}$ alkyl.

STARTING MATERIALS

Compounds of the formula I to be employed in the esterification method of the present invention, or compounds of the formula II to be employed in the hydrolysis method of the present invention, may be obtained by methods known to the skilled artisan. Such compounds are disclosed, for example, in U.S. Pat. Nos. 4,444,784, 3,983,140 and 4,346,227.

PREFERRED COMPOUNDS

Compounds of the formula I having the following formula Ia are preferred:

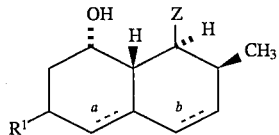

where Z, a and b are as defined in formula T and $R^1$ is hydrogen, hydroxyl or alkyl, especially trisubstituted $C_{1-6}$ alkyl such as methyl, or a salt thereof. Exemplary such compounds include the following compound:

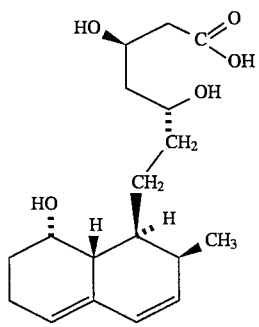

its partially or completely hydrogenated analogs where the a and/or b double bonds are absent, the corresponding compounds where Z is a lactone moiety and $R^3$ is hydroxyl, and alkali metal salts thereof.

Compounds of the formula II having the following formula IIa are preferred:

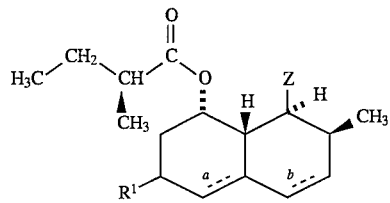

where Z, a and b are as defined in formula II and $R^1$ is hydrogen, hydroxyl or alkyl, especially unsubstituted $C_{1-6}$ alkyl such as methyl, or a salt thereof. Exemplary such compounds include the following:

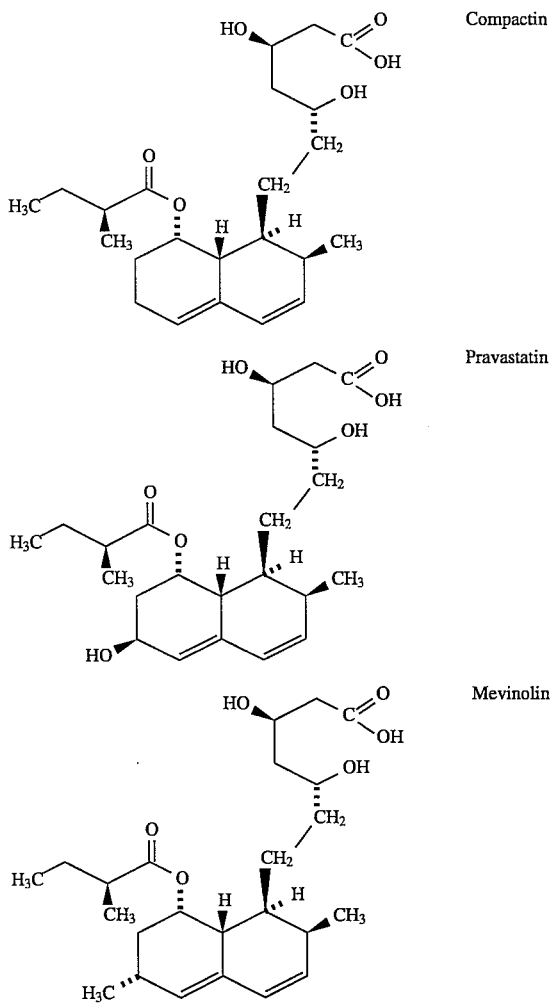

their partially or completely hydrogenated analogs where the a and/or b double bonds are absent, the corresponding compounds where Z is a lactone moiety and $R^3$ is hydroxyl, and alkali metal salts thereof.

The above structures shown for compactin, pravastatin and mevinolin are referred to herein as the acid form of these compounds. Where the carboxyl group of these compounds is in the alkali metal salt form, the compounds are referred to herein as the salt form of compactin, pravastatin and mevinolin. Likewise, the corresponding lactone forms of these compounds ($R^3$ is hydroxyl) are referred to herein as the lactone form of compactin, pravastatin and mevinolin.

As discussed below, the use of an aqueous medium is preferred in conducting the hydrolysis methods of the present invention. It is therefore preferred to prepare, or to employ as starting materials, those compounds of the formula I or II in which Z is the open chain moiety as defined above as such compounds are relatively more water soluble than the corresponding compounds in which Z is a lactone moiety. Compounds of the formula I or II in which Z is a lactone moiety may, for example, be hydrolyzed to the open chain form prior to use in the processes of the present invention.

ENZYMES AND MICROORGANISMS

The enzyme or microorganism employed in the methods of the present invention may be any enzyme or microorganism, regardless of origin or purity, having the ability to catalyze the conversions as described herein. Genera of microorganisms suitable as sources of catalyzing enzymes include *Penicillium, Aspergillus, Emericella, Kibdelosporangium, Chaetomium, Daldinia, Hypoxylan, Neurospora, Podospora, Sordaria, Xylaria, Cephalosporium, Gliocladium, Hypocrea, Nectria,* or *Trichoderma.*

Exemplary species suitable for use in the present processes include *Penicillium chrysogenum* such as ATCC 48271, *Aspergillus versicolor* such as ATCC 26268, *Emericella unguis* such as ATCC 34918, end the like. Particularly preferred are the actinomycete *Kibdelosporangium aridum* such as ATCC 39323, and the fungi *Penicillium turbatum* such as ATCC 28797, and *Chaetomium globosum* such as ATCC 44699.

With respect to the use of microorganisms, the methods of the present invention may be carried out using any microbial cellular material having the ability to catalyze the conversions as described herein. The cells may be used in the form of intact wet cells or dried cells such lyophilized, spray-dried or heat-dried cells. Cells may also be used in the form of treated cell material such as ruptured cells or cell extract. The cells or cellular materials, such as isolated fungal mycelia, may be employed in the free state or immobilized on a support such as by physical adsorption or entrapment. Two or more, as well as a single, species of microorganism may be employed when carrying out the instant processes. The term "ATCC" as used herein refers to the accession number of the American Type Culture Collection, 12301 Parklawn Drive, Rockville, Md. 20852, the depository for the organism referred to.

The methods of the present invention may be carried out subsequent to the growth of the microorganism(s) employed, for example, by growing the microorganisms either in the presence or absence of the formula I or II starting material, harvesting and, preferably, washing (e.g. with water) the microbial materials, and then contacting the microbial materials obtained with the formula I or II starting material. The methods of the present invention may also be carried out by in situ fermentation and reaction, that is, reaction in the presence of actively growing microorganisms.

The reaction may be conducted under quiescent (static) conditions, or by employing agitation. Agitation, such as shake-flask culture or aeration and agitation, is preferably employed when the formula I or II starting material is added to actively growing cultures. In such cases an anti-foaming agent may be employed.

The growth of microorganisms may be achieved by the skilled artisan, for example, by the use of an appropriate medium containing nutrients such as carbon and nitrogen sources and trace elements. Exemplary assimilable carbon sources include glucose, glycerol, maltose, dextrin, starch, lactose, sucrose, molasses, soybean oil, cotton seed oil, etc.; and exemplary assimilable nitrogen sources include soybean meal, peanut meal, cotton seed meal, fish meal, corn steep liquor, peptone, rice bran, meat extract, yeast, yeast extract, sodium nitrate, ammonium nitrate, ammonium sulfate, etc. Inorganic salts such as sodium chloride, phosphates, calcium carbonates, etc. may be added to the culture medium. A minor amount of a metal salt or heavy metal may also be added.

The same or different media may be employed at various stages of the growth of the microorganisms. Preferred media for the growth of microorganisms are those described in the examples herein, which media may be employed for the growth of any microorganism employed in the methods of the present invention.

Enzymes, when employed, are preferably derived from the aforementioned microorganisms, or may be synthetically or otherwise prepared, for example, derived from genetically engineered host cells. The use of the genetically engineered host cells themselves, or cells which have otherwise been modified, is also contemplated where such cells are capable of producing enzymes having the structure of enzymes derived from the above recited genera of microorganisms.

REACTION CONDITIONS

The methods of the present invention may be conducted in an aqueous medium, such as a buffered aqueous medium. The aqueous phase is conveniently of water, preferably deionized water, or a suitable aqueous buffer solution, especially a phosphate buffer solution. Use of an aqueous medium is preferred for the present hydrolysis methods.

The reactions of the present invention may also be conducted in an organic medium or in a medium which is a mixture of an organic medium and an aqueous medium. Use of an organic, or organic/aqueous medium may enhance solubilization of the less water soluble formula I or II starting materials, such as those where Z is a lactone moiety. Less water soluble starting materials may, for example, be dissolved in an organic solvent such as methyl or ethyl alcohol, and the solution added to an aqueous medium for conversion. Liquids forming such organic media may be immiscible in water or, preferably, may be miscible in water. Exemplary organic media include toluene, hexane, benzene, acetone, dimethylsulfoxide, cyclohexane, xylene, trichlorotrifluoroethane, alkanols such as methyl or ethyl alcohol or butanol, and the like. Use of organic or organic/aqueous media are preferred for the present esterification methods.

It is preferred that the starting materials are dissolved, for example, in water or an alcohol, prior to addition to the reaction medium.

The reaction medium preferably contains between about 0.5 to about 3 mg of formula I or II starting compound per ml of liquid medium. The pH of the reaction medium is preferably between about 6.0 and about 7.5.

To carry out the hydrolysis reaction of the present invention, water or an organic alcohol, for example, an alkanol such as methyl or ethyl alcohol, may be added. It is preferred to employ these materials in an amount providing a molar excess, preferably a large molar excess, based on the formula II starting material.

To carry out the esterification reaction of the present invention, 2-methylbutyric acid or esters thereof of the formula III are preferably added to provide a mole ratio of from about 33:1 to about 175:1 based on the amount of formula I starting material employed.

The amount of microbial cells added, where employed in the present processes, is preferably an amount ranging from about 10 to about 1000 mg per mg of formula I or II starting material.

The reaction medium is preferably held at a temperature between about 27° and 40° C., and is most preferably held between about 28° and about 34° C. The reaction time can be appropriately varied depending upon the amount of enzyme used and its specific activity. Typical reaction times are between about 2.5 hours and about 72 hours. Reaction times may be reduced by increasing the reaction temperature and/or increasing the amount of enzyme added to the reaction solution. Product yields are preferably obtained which are greater than about 90 mole % based on the starting substrate for the present hydrolysis process and greater than about 7 mole % based on the starting substrate for the present esterification process.

PREPARATION OF HMG-CoA REDUCTASE INHIBITORS

HMG-CoA reductase (3-hydroxy-3-methylglutaryl coenzyme A reductase) is a key enzyme in cholesterol biosynthesis. Inhibitors of this enzyme find utility as anticholesterolemic agents, that is, in lowering or maintaining plasma cholesterol levels. In addition to the treatment and prevention of hypercholesterolemia, HMG-CoA reductase inhibitors find utility in the treatment and prevention of atheroschlerosis, hyperlipoproteinaemia, and/or hyperlipidemia.

Compounds of the formulae I or II described above may themselves exhibit HMG-CoA reductase inhibiting activity (e.g. compactin, mevinolin and pravastatin), and/or may be employed as intermediates in the preparation of other compounds having HMG-CoA reductase inhibiting activity. In the latter case, the present invention further provides a method wherein hydrolysis or esterification is conducted according the above-described methods of the present invention and, subsequently, the hydrolyzed or esterified product so formed is employed in the preparation of an HMG-CoA reductase inhibitor (e.g., groups are deprotected, added or otherwise modified thereon). Preferably, the inhibitor so prepared has enhanced HMG-CoA reductase inhibiting activity relative to any such activity the hydrolyzed or esterified product from which it is prepared may possess.

A particularly preferred method for the preparation of an HMG-CoA reductase inhibitor of the present invention is that comprising the steps of:

(A) hydrolyzing a compound of the formula II, or a salt thereof, according to the above method of the present invention to yield a compound of the formula I:

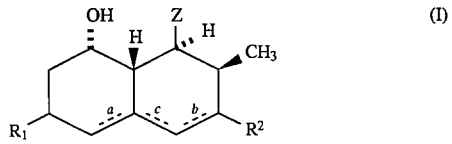

where Z, $R^1$, $R^2$, a, b and c are as defined above, or a salt thereof; and (B) esterifying the 8-position hydroxyl group of said compound I or salt thereof to yield a compound of the following formula IV:

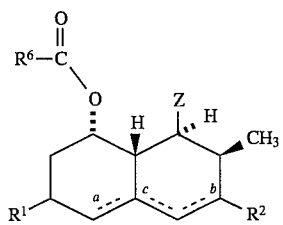

where Z, $R^1$, $R^2$, a, b and c and $R^6$ is alkyl, such as $C_{1-10}$ unsubstituted alkyl, $C_{1-10}$ $CF_3$-substituted alkyl, unsubstituted phenyl-$C_{1-3}$ alkyl or substituted phenyl-$C_{1-3}$ alkyl in which the substituent is halo, $C_{1-3}$ alkyl or $C_{1-3}$ alkoxy; cycloalkyl such as $C_{3-10}$ unsubstituted cycloalkyl; alkenyl such as $C_{2-10}$ unsubstituted alkenyl; or aryl, such as unsubstituted phenyl or halophenyl, or a salt thereof.

Preferred compounds of the formula IV are those where $R^6$ is $C_{1-10}$ unsubstituted alkyl, particularly where $R^6$ is:

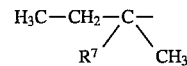

where $R^7$ is alkyl, especially methyl. Exemplary compounds IV include synvinolin, having the structure:

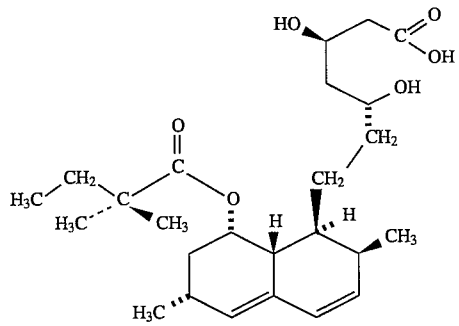

or methyl pravastatin having the structure:

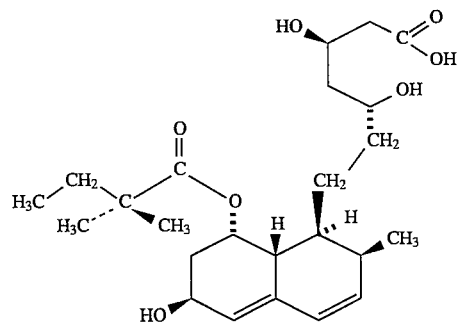

the alkali metal, especially sodium or lithium salts thereof, and the corresponding compounds where Z is a lactone moiety and $R^3$ is hydroxyl.

Other exemplary HMG-CoA reductase inhibitors which may be prepared by this embodiment of the invention include those compounds described in U.S. Pat. No. 4,444,784, incorporated herein by reference.

The above step (B) may be conducted by contacting the compound I with a carboxylic acid of the formula:

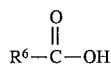

under conditions suitable for achieving the esterification reaction, for example, in the presence of a carbodiimide such as N,N'-dicyclohexylcarbodiimide with 4-pyrrolidinopyridine as a catalyst in a solvent such as dichloromethane. The above step (B) may also be conducted by contacting the compound I with an acid chloride of the formula:

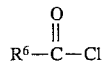

under conditions suitable for achieving the esterification reaction, for example, in pyridine in the presence of 4-dimethylaminopyridine as a catalyst. Hydroxyl groups present which are not to be reacted are preferably protected when conducting step (B).

The above step (B), where $R^6$ is (1-methyl)propyl (—CH($CH_3$)—$CH_2$—$CH_3$), may also be conducted by the present enzymatic esterification method.

Compounds of the formula IV, or any compound described herein, in which one or more of the a, b or c double bonds is absent, may be obtained by hydrogenating the corresponding compound in which such bonds are present according to methods known to the skilled artisan.

Any of the products of the present methods may be isolated and purified by known methodologies such as by filtering off cells or cellular materials where appropriate, extraction, crystallization, thin layer or column chromatography, high performance liquid chromatography and the like.

HMG-CoA reductase inhibitors obtained according to the methods of the present invention may, for example, be administered to mammals, particularly humans, by modes and in dosages selected according to methods known to the skilled artisan.

The following Examples illustrate preferred embodiments of the present invention, and are not intended to limit the scope or spirit of the instant claims. The components of the media employed in these Examples are as follows.

| Medium | Media Compositions |
| --- | --- |
| K15 | baby oatmeal food 20 g/L, Contadina tomato paste 20 g/L, tap water to one liter, adjust pH to 7.0 |
| A55 | peptone 15 g/L, spray-dried corn steep liquor 3 g/L, cerelose 50 g/L, tap water to one liter, adjust pH to 6.5 |
| A94 | spray-dried corn steep liquor 17.5 g/L, cerelose 20 g/L, $(NH_4)_2SO_4$ 5 g/L, $CaCO_3$ 3.5 g/L, soybean oil 5 ml/L, distilled water to one liter |
| K28 | Pharmamedia 25 g/L, cerelose 69 g/L, $CaCO_3$ 9 g/L, $K_2HPO_4$ 0.1 g/L, Ucon antifoam 0.5 g/L, tap water to one liter, adjust pH to 6.8–7.0 |
| JES | glucose 10 g/L, peptone 2 g/L, beef extract 1 g/L, spray-dried corn steep liquor 1 g/L, distilled water to one liter |
| AT-1 | cerelose 49.5 g/L, peptonized milk 24 g/L, yeast extract 2.5 g/L, distilled water to one liter |
| F7 | malt extract 10 g/L, yeast extract 10 g/L, peptone 1 g/L, dextrose 20 g/L, distilled water to one liter, adjust pH to 7.0 |

-continued

| Medium | Media Compositions |
| --- | --- |
| K28 modif. | Pharmamedia 7 g/L, cerelose 69 g/L, peptone 5 g/L, $CaCO_3$ 9 g/L, $K_2HPO_4$ 0.1 g/L, tap water to one liter, adjust pH to 6.8–7.0 |
| DPY | glucose 20 g/L, peptone 10 g/L, yeast extract 1 g/L, distilled water to one liter |
| F4 | tryptone 5 g/L, malt extract 3 g/L, glucose 10 g/L, yeast extract 3 g/L, distilled water to one liter |

EXAMPLE 1

Hydrolysis of the lactone and water soluble sodium salt forms of compactin was conducted as follows:

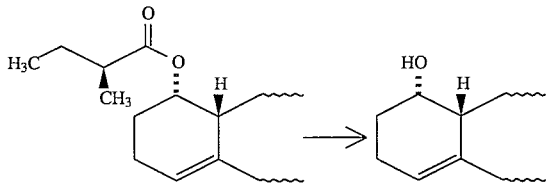

Shake-Flask Procedure—*Kibdelosporangium aridum* ATCC 39323

A frozen vial of *Kibdelosporangium aridum* ATCC 39323 was thawed and used to inoculate a 500 ml flask containing 100 ml of medium K15. The flask was placed on a shaker at approximately 280 rpm, at 25° C., and shaken for 72 hours. Aliquots of 2.5 ml apiece of the 72 hour culture broth were used to inoculate 250 ml flasks containing 50 ml of medium A55. These flasks were shaken at approximately 280 rpm, at 25°.

After 24 hours of shaking, either compactin salt or compactin lactone was added aseptically to each flask. The salt was added as an aqueous solution. The lactone was dissolved in a minimal volume of ethanol, and formed a fine white precipitate upon addition to the broths. Final concentration of compactin in the flasks was 250 µg/ml, both for flasks which received salt and for flasks which received lactone. Shaking was resumed for an additional 24 hours. All flasks then received a second 250 µg/ml dose of compactin; flasks which had previously received lactone were given a second lactone dose, and flasks which had previously received the salt were given a second salt dose. Shaking was resumed for 24 hours, following which half of the flasks were harvested and their broths submitted for assay of compactin substrate and hydrolyzed compactin product. The remaining flasks were harvested and their broths submitted for assay following an additional 24 hours of shaking.

Isolated Cell, Static Procedure—*Kibdelosporangium aridum* ATCC 39323

*K. aridum* cells were grown by the shake-flask procedure detailed above, except that an additional group of culture broths in medium A55 received no compactin substrate. These were subsequently referred to as "non-induced" cells, while cells which had been exposed to compactin substrate were subsequently referred to as "induced" cells.

After 72 hours in medium A55, induced and non-induced cells were collected separately. Collection was by centrifugation of the whole broths, followed by a water wash and a second centrifugation. Three grams of damp, packed cells were added to a reaction mixture containing 4 ml of 0.2M pH 7.5 phosphate buffer, 0.1 ml of 60 mg/ml compactin lactone dissolved in ethanol, and 4.9 ml of distilled water. Non-induced and lactone-induced cells were added to different reaction mixtures. Reaction mixtures were initially thoroughly mixed, then were incubated statically for 16 hours at 32° C., and were then submitted for analysis of compactin substrate and hydrolyzed compactin product.

Shake-Flask Procedure—*Chaetomium globosum* ATCC 44699

A frozen vial of *Chaetomium globosum* ATCC 44699 was thawed and used to inoculate a 500 ml flask containing 100 ml of medium A94. The flask was placed on a shaker at approximately 280 rpm, at 25° C., and shaken for 72 hours. Aliquots of 2.5 ml apiece of the 72 hour culture broth were used to inoculate 250 ml flasks containing 50 ml of medium K28. These flasks were shaken at approximately 280 rpm, at 25° C.

After 24 hours of shaking, either compactin salt or compactin lactone was added aseptically to each flask. The salt was added as an aqueous solution. The lactone was dissolved in a minimal volume of ethanol, and formed a fine white precipitate upon addition to the broths. Final concentration of compactin substrate in the flasks was 250 µg/ml, both for flasks which received salt and flasks which received lactone. Shaking was resumed for an additional 24 hours. All flasks then received a second 250 µg/ml dose of compactin substrate; flasks which had previously received lactone were given a second lactone dose, and flasks which had previously received the salt were given a second salt dose. Shaking was resumed for 24 hours, following which half of the flasks were harvested and their broths submitted for assay of compactin substrate and hydrolyzed compactin product. The remaining flasks were harvested and their broths submitted for assay following an additional 24 hours of shaking.

Isolated Cell, Static Procedure—*Chaetomium globosum* ATCC 44699

*C. globosum* was grown by the shake-flask procedure detailed above, except that an additional group of culture broths in medium K28 received no compactin substrate. These were subsequently referred to as "non-induced" cells, while cells which had been exposed to compactin substrate were subsequently referred to as "induced" cells.

After 72 hours in medium K28, induced and non-induced cells were collected separately. Collection was by filtration of the whole broths. Three grams of damp cells were added to a reaction mixture containing 4 ml of 0.2M pH 7.5 phosphate buffer, 0.1 ml of 60 mg/ml compactin lactone dissolved in ethanol, and 4.9 ml of distilled water. Non-induced and lactone-induced cells were added to different reaction mixtures. Reaction mixtures initially were thoroughly mixed, then were incubated statically 16 hours at 32° C., and were then submitted for analysis of compactin substrate and hydrolyzed compactin product.

The results obtained by the above procedures are shown in Table 1 following.

TABLE 1

Hydrolysis of 500 µg/ml compactin lactone[1] and soluble salt

| Substrate Form | Reaction Method | Reaction Time (Hours)[2] | Substrate[3] S1[5] | S2 | Product[4] S1 | S2 |
|---|---|---|---|---|---|---|
| Culture: *Kibdelosporangium aridum* ATCC 39323 | | | | | | |
| lactone | shake flask | 48 | 15 | 18 | 136 | 118 |
| lactone | shake flask[6] | 72 | 45 | 2 | 25 | 116 |
| lactone | isolated cell[7] | 16 | 41 | 33 | 324 | 432 |
| salt | shake flask | 48 | 0 | 0 | 326 | 249 |
| salt | shake flask | 72 | 0 | 0 | 213 | 136 |
| Culture: *Chaetomium globosum* ATCC 44699 | | | | | | |
| lactone | shake flask | 48 | 145 | 129 | 144 | 147 |
| lactone | shake flask | 72 | 86 | 71 | 211 | 211 |
| lactone | isolated cell[7] | 16 | 121 | 277 | 49 | 81 |
| salt | shake flask | 48 | 0 | 0 | 537 | 673 |
| salt | shake flask | 72 | 0 | 0 | 759 | 946 |

[1]Compactin breakdown products also noted, for lactone only.
[2]Number of hours substrate in contact with microbial material. (First substrate addition to shake-flask culture was made when cells were 24 hours old.)
[3]µg compactin lactone or salt per ml sample remaining.
[4]µg hydrolyzed product per ml sample.
[5]S1 = sample from flask no. 1; S2 = sample from flask no. 2.
[6]Fungal contamination was noted.
[7]S1 = non-induced cells; S2 = induced cells; for isolated cell reaction method only.

As can be seen from Table 1 above, the salt form was completely hydrolyzed. Over 60% complete hydrolysis of the lactone form was obtained using the *K. aridum* isolated cells, and about 40% complete hydrolysis was obtained using *C. globosum* in shake flasks.

EXAMPLE 2

Hydrolysis of the lactone form of mevinolin was conducted as follows:

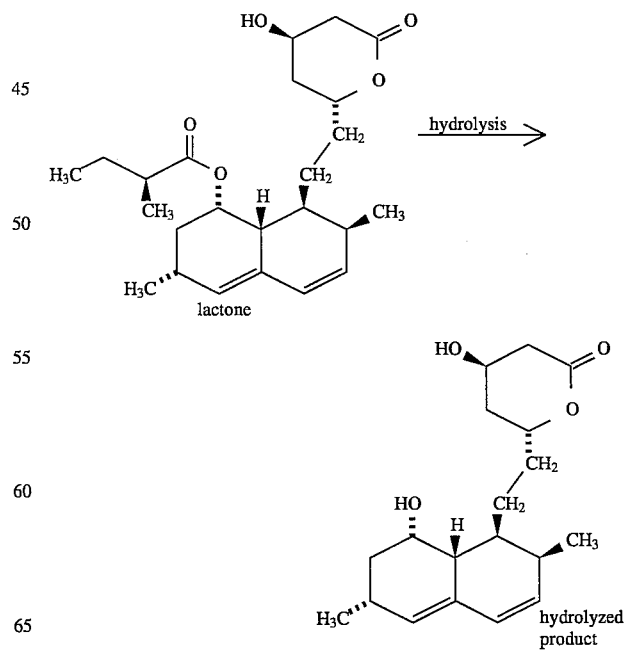

Shake-Flask Procedure—*Kibdelosporangium aridum* ATCC 39323

A frozen vial of *Kibdelosporangium aridum* ATCC 39323 was thawed and used to inoculate a 500 ml flask containing 100 ml of medium K15. The flask was placed on a shaker at approximately 280 rpm, at 25° C., and shaken for 72 hours. Aliquots of 2.5 ml apiece of the 72 hour culture broth were used to inoculate 250 ml flasks containing 50 ml of medium A55. These flasks were shaken at approximately 280 rpm, at 25° C.

After 24 hours of shaking, mevinolin lactone was added aseptically to each flask. The lactone was dissolved in a minimal volume of ethanol, and was added to a final concentration in the culture broth of 250 µg/ml. Shaking was resumed for an additional 24 hours. All flasks then received a second 250 µg/ml dose of mevinolin lactone. Shaking was resumed for 24 hours, following which half of the flasks were harvested and their broths submitted for assay of mevinolin substrate and hydrolyzed mevinolin product. The remaining flasks were harvested and their broths submitted for assay following an additional 24 hours of shaking.

Isolated Cell, Static Procedure—*Kibdelosporangium aridum* ATCC 39323

*K. aridum* cells were grown by the shake-flask procedure detailed above, except that an additional group of culture broths in medium A55 received no mevinolin substrate. These were subsequently referred to as "non-induced" cells, while cells which had been exposed to mevinolin substrate were subsequently referred to as "induced" cells.

After 72 hours in medium A55, induced and non-induced cells were collected separately. Collection was by centrifugation of the whole broths, followed by a water wash and a second centrifugation. Three grams of damp, packed cells were added to a reaction mixture containing 4 ml of 0.2M pH 7.5 phosphate buffer, 0.1 ml of 60 mg/ml mevinolin lactone dissolved in ethanol, and 4.9 ml of distilled water. Non-induced and mevinolin-induced cells were added to different reaction mixtures. Reaction mixtures were initially thoroughly mixed, then were incubated statically for 16 hours at 32° C., and were then submitted for analysis of mevinolin substrate and hydrolyzed mevinolin product.

Shake-Flask Procedure—*Chaetomium globosum* ATCC 44699

A frozen vial of *Chaetomium globosum* ATCC 44699 was thawed and used to inoculate a 500 ml flask containing 100 ml of medium A94. The flask was placed on a shaker at approximately 280 rpm, at 25° C., and shaken for 72 hours. Aliquots of 2.5 ml apiece of the 72 hour culture broths were used to inoculate 250 ml flasks containing 50 ml of medium K28. These flasks were shaken at approximately 280 rpm, at 25° C.

After 24 hours of shaking, mevinolin lactone was added aseptically to each flask. The lactone was dissolved in a minimal volume of ethanol, and was added to a final concentration of 250 µg/ml in the culture broth. Shaking was resumed for an additional 24 hours. All flasks then received a second 250 µg/ml dose of mevinolin lactone. Shaking was resumed for 24 hours, following which half of the flasks were harvested and their broths submitted for assay of mevinolin substrate and hydrolyzed mevinolin product. The remaining flasks were harvested and their broths submitted for assay following an additional 24 hours of shaking.

Isolated Cell, Static Procedure—*Chaetomium globosum* ATCC 44699

*C. globosum* cells were grown by the shake-flask procedure detailed above, except that an additional group of culture broths of medium K28 received no mevinolin substrate. These were subsequently referred to as "non-induced" cells, while cells which had been exposed to mevinolin substrate were subsequently referred to as "induced" cells.

After 72 hours in medium K28, induced and non-induced cells were collected separately by filtration. Three grams of damp cells were added to reaction mixtures containing 4 ml of 0.2M pH 7.5 phosphate buffer, 0.1 ml of 60 mg/ml mevinolin lactone dissolved in ethanol, and 4.9 ml of distilled water. Non-induced and mevinolin-induced cells were added to different reaction mixtures. Reaction mixtures initially were thoroughly mixed, then were incubated statically for 16 hours at 32° C.; and were then submitted for analysis of mevinolin substrate and hydrolyzed mevinolin product.

The results obtained by the above procedures are shown in Table 2 following.

TABLE 2

Hydrolysis of 500 µg/ml mevinolin lactone[1]

| Reaction Method | Reaction Time (Hours)[2] | Substrate[3] S1[5] | S2 | Product[4] S1 | S2 |
|---|---|---|---|---|---|
| Culture: *Kibdelosporangium aridum* ATCC 39323 | | | | | |
| shake flask | 48 | 153 | 71 | 0 | 20 |
| shake flask[6] | 72 | 57 | 150 | 0 | 0 |
| isolated cell[7] | 16 | 61 | 65 | 273 | 332 |
| Culture: *Chaetomium globosum* ATCC 44699 | | | | | |
| shake flask | 48 | 156 | 151 | 140 | 134 |
| shake flask | 72 | 139 | 290 | 208 | 187 |
| isolated cell[7] | 16 | 111 | 221 | 62 | 68 |

[1]Mevinolin breakdown products also noted in some samples.
[2]Number of hours substrate in contact with microbial material. (First substrate addition to shake-flask cultures was made when cells were 24 hours old.)
[3]µg mevinolin lactone per ml sample remaining.
[4]µg hydrolyzed product per ml sample.
[5]S1 = sample from flask no. 1; S2 = sample from flask no. 2.
[6]Fungal contamination was noted.
[7]S1 = non-induced cells; S2 = induced cells; for isolated cell reaction method only.

As can be seen from Table 2 above, the isolated cells of *K. aridum* were the most active, followed by *C. globosum* shake flasks.

EXAMPLE 3

Fungus, selected from *Penicillium turbatum* ATCC 28797 or *Chaetomium globosum* ATCC 44699, was inoculated from slant or frozen vial into 500 ml germinator flasks containing 100 ml of the growth medium A94. Flasks were shaken at 280 rpm for 72 hours at 25° C. 7.5 ml of germinator flask broth was used to inoculate 500 ml bioconversion flasks containing 100 ml of the medium set forth in Tables 3 and 4. These flasks were shaken at the same speed (280 rpm) and temperature (25° C.). An inhibitor selected from the sodium salt form of pravastatin, mevinolin or compactin was added to a final concentration set forth in Tables 3 and 4 when the bioconversion culture was 24 hours old. Samples were taken for analysis 24 and 48 hours later.

The fungi employed were found to hydrolyze all three inhibitors added. Substrate conversion was raised to 100% by changing the bioconversion medium to suit each organism. The results obtained at 48 hours are presented in the following Tables 3 and 4.

TABLE 3

*Penicillium turbatum*: Side Chain Removal From Three Inhibitors (Salt Form) by Shake Flask Cultures

| Substrate Inhibitor | Inhibitor Conc., mg/ml | Bioconv. Medium | Substrate Conversion- Side Chain Removal |
|---|---|---|---|
| Pravastatin | 500 | A55 | 82% |
|  | 500 | A94 | 17% |
|  | 500 | F7 | 100% |
|  | 500 | JES | 69% |
|  | 500 | K28 | 88% |
| Mevinolin | 500 | F7 | 100% |
| Compactin | 1000 | F7 | 100% |
|  | 1000 | JES | 68% |
|  | 1000 | K28 | 100% |
|  | 1000 | K28 MODIF. | 98% |

TABLE 4

*Chaetomium globosum*: Side Chain Removal From Three Inhibitors (Salt Form) by Shake Flask Cultures

| Substrate Inhibitor | Inhibitor Conc., μg/ml | Bioconv. Medium | Substrate Conversion- Side Chain Removal |
|---|---|---|---|
| Pravastatin | 500 | K28 | 100% |
|  | 1000 | K28 | 99% |
|  | 1500 | K28 | 63% |
|  | 2000 | K28 | 67% |
|  | 2500 | K28 | 56% |
|  | 500 | A55 | 67% |
|  | 500 | AT-1 | 49% |
|  | 500 | F7 | 67% |
|  | 500 | JES | 4% |
| Mevinolin | 500 | K28 | 100% |
| Compactin | 1000 | K28 | 100% |
|  | 2000 | K28 | 96% |
|  | 3000 | K28 | 72% |

EXAMPLE 4

Side Chain Removal by *Kibdelosporangium aridum*

Procedure for Side Chain Removal by *Kibdelosporangium aridum* Shake-Flask Cultures A slant of *K. aridum* ATCC 39323 was used to inoculate a 250 ml flask containing 50 ml of medium F4. The flask was shaken at approximately 280 rpm at 25° for 72 hours.

Aliquots of 3 ml of the 72 hour F4 broth were used to inoculate 250 ml flasks containing 50 ml either of medium DPY or K28. These flasks then were shaken at approximately 280 rpm at 25° C. After 24 hours of shaking, the sodium salt form of compactin was aseptically added to each flask to a final broth concentration of 500 μg/ml. Shaking was then resumed for 24 hours, after which each flask received an additional 1000 μg/ml dose of compactin substrate. Shaking was then resumed for 48 hours, at which time the flasks were harvested and their broths were submitted for assay of compactin substrate and hydrolyzed compactin product.

The results which were obtained are shown in the following Table 5.

TABLE 5

*Kibdelosporangium aridum*: Side Chain Removal From Compactin (Salt Form) by Shake Flask Cultures

| Substrate Inhibitor | Inhibitor Conc., μg/ml | Bioconv. Medium | Substrate Conversion- Degree of Side Chain Removal |
|---|---|---|---|
| Compactin | 1500 | DPY | 68% |
|  | 1500 | K28 | 100% |

EXAMPLE 5

Side Chain Removal by Isolated Mycelium

Forty-eight hr. mycelium of *C. globosum* ATCC 44699 in medium K28 was harvested by filtration, washed, and added at 0.25 g/ml to a pH 7.5 reaction mixture containing 0.1M pH 7.5 phosphate buffer (10 ml), distilled water (4.8 ml), *C. globosum* cells (5 g) and pravastatin (sodium salt form) (60 mg/ml solution, 0.17 ml added to yield 500 μg/ml pravastatin salt).

Seventy-two hr. mycelium of *K. aridum* ATCC 39323 in medium A55 was harvested by centrifugation, washed, and added at 0.3 g/ml to a pH 7.5 reaction mixture containing either compactin (sodium salt form) or mevinolin (sodium salt form). The compactin salt reaction medium contained: 0.2M pH 7.5 phosphate buffer (4 ml), *K. aridum* cells (4 g), distilled water (3.9 ml), compactin (salt form) (60 mg/ml solution, 0.1 ml added to yield 500 μg/ml compactin salt). The mevinolin salt reaction medium contained: 0.2M pH 7.5 phosphate buffer (4 ml), distilled water (3.75 ml), *K. aridum* cells (3.5 g), mevinolin (salt form) (2.4 mg/ml solution, 0.75 ml added to yield 150 μg/ml mevinolin salt).

Incubation was at 32° C. with daily sampling until conversion was complete. The results obtained are presented in the following Table 6.

TABLE 6

Side Chain Removal by Isolated Mycelium In Static Incubation

| Culture | Inhibitor (Salt Form) | Inhibitor Conc., μg/ml | Conversion at 16 hours |
|---|---|---|---|
| *C. globosum**  | pravastatin | 500 | 100% (complete in 2.5 hr) |
| *C. globosum*** | pravastatin | 500 | 100% (complete in 2.5 hr) |
| *K. aridum**   | compactin | 500 | 100% |
| *K. aridum***  | compactin | 500 | 100% |
| *K. aridum***  | mevinolin | 150 | 52% (complete by 64 hr) |

*exposed - inhibitor was added to the shake-flasks during the growth phase.
**non-exposed - mycelium had no exposure to inhibitor until static incubation.

EXAMPLE 6

Esterification of Side Chain-free Compactin

Side chain-free compactin having the following structure was obtained by removal of the methylbutyrate side chain from compactin:

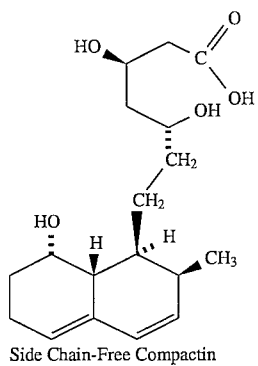

Side Chain-Free Compactin

Enzymatic esterification of the 8-position hydroxyl group of this compound was conducted by employing *Kibdelosporangium aridum* ATCC 39323 mycelium and methylbutyrate methyl ester as the compound III (methylbutyric acid was inactive in the system employed).

A "standard" reaction mixture having the following components:

pH 5.5 2-(N-morpholino)ethanesulfonic acid (MES) buffer, final strength 0.07M methylbutyrate methyl ester, 33 mg/ml side chain-free compactin, 1 mg/ml washed *K. aridum* mycelium, 0.3 g/ml distilled water was incubated at 32° C., overnight. The results obtained are presented in the following Table 7. Also presented in Table 7 are the results obtained upon the addition of a number of organic solvents in the amounts specified.

TABLE 7

*Kibdelsporangium aridum*: Replacement of Side Chain on De-esterified Compactin

| Sample | Amt of Solvent added | Compactin Formed, μg/ml | % Product Formation |
|---|---|---|---|
| Neg. Control no cells | — | 0 | none |
| Neg. Control no MB-ME | — | 0 | none |
| Standard | — | 29 | 5% |
| Std-acetone added | 1 ml | 19 | 3% |
| Std-butanol added | 2.5 ml | 0 | none |
| Std-DMSO added | 1 ml | 26 | 4% |
| Std-ethanol added | 1 ml | 12 | 2% |
| Std-hexane added | 2.5 ml | 3 | 0.5% |
| Std-methanol added | 1 ml | 17 | 3% |
| Std-toluene added | 2.5 ml | 4 | 0.6% |

*MB-ME = a methylbutyrate methyl ester
Std = "standard" reaction medium
DMSO = dimethylsulfoxide

What we claim is:

1. A method for the preparation of a compound of the formula I:

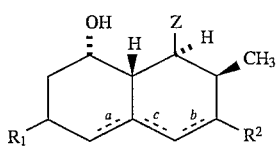

where

Z is the lactone:

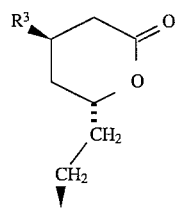

or the open chain moiety:

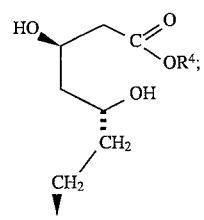

$R^1$ and $R^2$ are independently selected from:
(i) hydrogen;
(ii) hydroxyl;
(iii) alkoxy;
(iv) alkyl;
(v) —$OSO_2H$; or
(vi) if not already included above, protected hydroxyl;

$R^3$ is hydroxyl or protected hydroxyl;

$R^4$ is hydrogen; a pharmaceutically acceptable cation; or a moiety which, together with the atoms to which it is bonded, forms a pharmaceutically acceptable ester group; and a, b and c represent optional double bonds which double bonds, when any are present, are a and b in combination or a, b or c alone; or a salt thereof;

comprising the step of contacting a compound of the formula II:

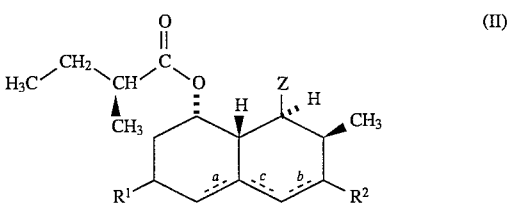

where Z, $R^1$, $R^2$, a, b and c are as defined in formula I, or a salt thereof, with a microorganism, or with an enzyme derived from, or having the structure of an enzyme derived from, said microorganism, which is capable of catalyzing the hydrolysis of said compound of the formula II or salt thereof to yield said compound of the formula I or salt thereof, and effecting said hydrolysis;

where said microorganism is selected from the genera *Penicillium*, *Kibdelosporangium*, *Chaetomium*, *Aspergillus*, *Emericella*, *Daldinia*, *Hypoxylan*, *Neurospora*, *Podospora*, *Sordaria*, *Xylaria*, *Cephalosporium*, *Gliocladium*, *Hypocrea*, *Nectria* or *Trichoderma*, with the proviso that said microorganism is not *Emericella unguis* when, in formulae I and II, the double bonds a and b are present, $R^1$ is hydrogen or methyl, and $R^2$ is hydrogen.

2. The method of claim 1, wherein Z is said open chain moiety.

3. The method of claim 1, wherein a compound having the following formula Ia is prepared:

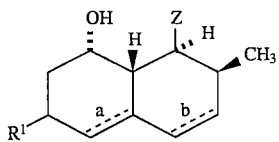 (Ia)

where Z, a and b are as defined in formula I and $R^1$ is hydrogen, hydroxyl or alkyl, or a salt thereof.

4. The method of claim 3, wherein said compound of the formula Ia is:

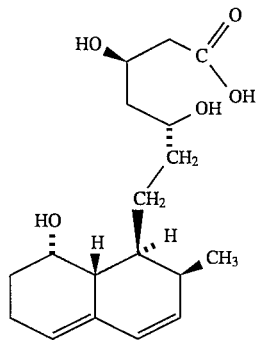

its partially or completely hydrogenated analogs where the a and/or b double bonds are absent, the corresponding compounds where Z is a lactone moiety and $R^3$ is hydroxyl, and alkali metal salts thereof.

5. The method of claim 1, wherein said microorganism is *Penicillium chrysogenum* ATCC 48271, *Aspergillus versicolor* ATCC 26268, or *Emericella unguis* ATCC 34918.

6. The method of claim 1, wherein said microorganism is selected from *Kibdelosporangium aridum* ATCC 39323, *Penicillium turbatum* ATCC 28797 or *Chaetomium globosum* ATCC 44699.

7. The method of claim 1, wherein said hydrolysis is conducted in an aqueous medium.

* * * * *